(12) United States Patent
Chien

(10) Patent No.: US 9,732,921 B2
(45) Date of Patent: Aug. 15, 2017

(54) MULTIPLE FUNCTIONS WALL COVER PLATE HAS BUILT-IN USB AND LIGHT MEANS

(71) Applicant: Tseng-Lu Chien, Walnut, CA (US)

(72) Inventor: Tseng-Lu Chien, Walnut, CA (US)

( * ) Notice: Subject to any disclaimer, the term of this patent is extended or adjusted under 35 U.S.C. 154(b) by 2 days.

(21) Appl. No.: 13/910,295

(22) Filed: Jun. 5, 2013

(65) Prior Publication Data

US 2014/0362559 A1    Dec. 11, 2014

(51) Int. Cl.
```
F21S 8/00      (2006.01)
F21V 33/00     (2006.01)
F21V 23/04     (2006.01)
H02G 3/14      (2006.01)
H02G 3/18      (2006.01)
A61L 9/03      (2006.01)
```

(52) U.S. Cl.
CPC .......... F21S 8/033 (2013.01); A61L 9/03 (2013.01); F21V 23/0442 (2013.01); F21V 33/00 (2013.01); H02G 3/14 (2013.01); H02G 3/18 (2013.01); A61L 2209/111 (2013.01); A61L 2209/12 (2013.01); A61L 2209/133 (2013.01)

(58) Field of Classification Search
CPC ......... F21S 8/035; F21V 23/0442; H02G 3/18
USPC ............... 362/95; 200/293, 294, 296
See application file for complete search history.

(56) References Cited

U.S. PATENT DOCUMENTS

| | | | | |
|---|---|---|---|---|
| 3,297,886 A | * | 1/1967 | Danner | 307/112 |
| 6,540,554 B2 | * | 4/2003 | McCarthy | 439/574 |
| 7,318,653 B2 | * | 1/2008 | Chien | 362/95 |
| 7,338,328 B2 | * | 3/2008 | Krieger | B60R 11/02 439/668 |
| 7,997,925 B2 | * | 8/2011 | Lam | H01R 13/665 174/66 |
| 8,439,692 B1 | * | 5/2013 | Oddsen | H01R 25/006 439/107 |
| 2008/0012423 A1 | * | 1/2008 | Mimran | H01R 25/003 307/11 |
| 2009/0315509 A1 | * | 12/2009 | Wu | 320/107 |
| 2012/0276763 A1 | * | 11/2012 | Quezada | H01R 13/665 439/108 |
| 2012/0292991 A1 | * | 11/2012 | Dodal | H02H 3/16 307/11 |

* cited by examiner

*Primary Examiner* — Elmito Breval
(74) *Attorney, Agent, or Firm* — Bacon & Thomas, PLLC

(57) ABSTRACT

The multiple functions wall cover plate has built-in USB and light means connect by prong means to existing wall inner-kit's receptacle to get AC power source to multiple function wall cover's circuit(s) to drive each circuit for predetermined functions. The said cover plate fasten by screw, prong or false prong to hold on inner-kit's holder and overlay at least one of the inner receptacle to offer people safety and quickly USB charger with desire light illumination and add extra functions.

11 Claims, 8 Drawing Sheets

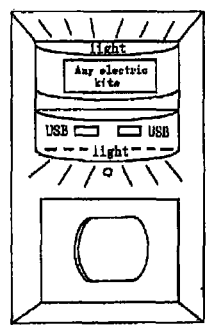 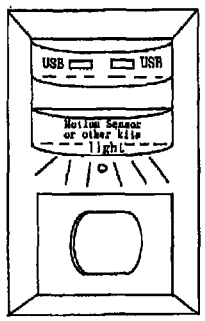 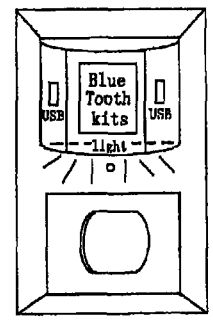
Fig. 4　　　Fig. 5　　　Fig. 6
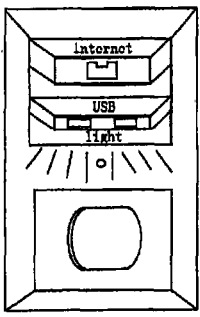 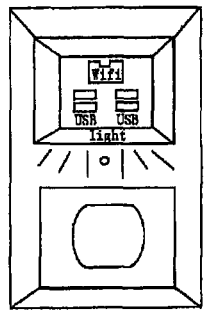 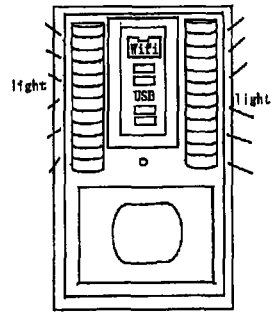
Fig. 7　　　Fig. 8　　　Fig. 9

MULTIPLE FUNCTIONS WALL COVER PLATE HAS BUILT-IN USB AND LIGHT MEANS

BACKGROUND OF THE INVENTION

This application has subject matter in common with the inventor's U.S. Pat. No. 7,318,653, which discloses built-in outlets and light means on a wall plate cover.

The current invention for USB charger related products may utilize the built-in liquid and display unit disclosed in the inventor's prior U.S. Pat. No. 5,926,440 and U.S. Pat. No. 7,909,477, for a liquid with medium-means, decorative-means, or miniature-means within a container for different light sources.

The current invention also has subject matter in common with the inventor's U.S. patent application Ser. No. 13/870, 253, which is directed to a wire arrangement for hand-reachable desktop USB charger related products, and which was filed on Apr. 22, 2013.

The current invention also has subject matter in common with the inventor's U.S. patent application Ser. No. 13/863, 073, which is directed to a power station or products having built-in USB & LED unit(s) for desk top installation, which was filed on Apr. 15, 2013.

The current invention also has subject matter in common with the inventor's U.S. patent application Ser. No. 13/858, 046, for a wire arrangement for a USB charger device which has an add-on or built-in wire arrange-means, and which was filed on Apr. 8, 2013.

The current invention also has subject matter in common with the inventor's U.S. patent application Ser. No. 13/161, 643, filed on May 27, 2011, and directed to a desk top LED device having a USB unit to charge other electric or digital data device(s).

The current invention also has subject matter in common with the inventor's U.S. patent application Ser. No. 13/117, 227 filed on May 27, 2011, which is directed to a universal module for a USB unit and/or outlet-unit for electric or digital data device(s).

The current invention is also has subject matter in common with the inventor's U.S. patent Ser. No. 12/950,017, which is directed to a multiple surface LED light having USB/Outlets/LED.

The above-cited patent applications disclose desktop hand-reachable USB-charger related products having wire-arrangements so that the wires for receiving-means including USB-ports, outlet receiving sockets, LED-units or any combinations thereof have wire arrangements that provide people with convenient hand-reachable chargers or power on a desk surface (including a desktop or other surface).

The present invention provides various improvement, including:

1. The USB and light means are installed within a multiple function cover plate, which will make the device thinner and more compact in size than a plug-in type overlay for an existing wall cover plate.
2. No built-in wire arrangement to coil, wrap, roll, store, or release AC power wires or other wires related to USB charger operation is needed, resulting in no more mess involving AC wires or other wires for charging kits such as the one disclosed in copending U.S. patent application Ser. No. 13/858,046.
3. The basic model has a built-in USB port and light means selected from all kinds of market-available light means that not only can charge another electric or digital data device but also offer a light means. An LED light means including more than one LED, as disclosed in various prior patents and publication of the inventor, is preferred. The light means may also include or be associated with more than one optics means, more than one function, more than one reflective means, and and/or other features disclosed in the inventor's patents and patent application to cause the LED light means to have the best light performance.
4. The wall plate cover of the invention may be optionally made into a flat and big size, thin product to underlay all or at least one of the existing wall outlet receptacle(s) and optionally provide a built-in plurality of outlets to enable people to have more outlets and connect with more external electric or digital data devices.
5. The USB charger output-end power min. has 1.0 Amp up to N-Amp, which cannot be obtained from laptop USB ports or other portable or travel USB chargers. As a result, there is no need to wait a long time to charge electric or electronic devices so as to save people time to fully charge all electric or digital data device(s).
6. A wire arrangement by roller, retractable means, spring means, or twist means can be provided to allow people keep all charging-related wires or AC power wires well stored and not make a mess.

Finally, this application also has subject matter in common with the inventor's U.S. patent application Ser. No. 10/954,189 filed Oct. 1, 2004 and now abandoned, which was directed to an electroluminescent wall cover plate.

The current invention provides improvements to the inventor's previously disclosed wall cover having built-in light source by adding receiving-means including any combination of a USB charger, AC power sources, and optional other electric devices.

A multiple function wall cover plate has been disclosed in several prior patents, including U.S. Pat. Nos. 6,714,725, 6,810,204, 6,832,794, and 6,839,506, but the prior multiple function wall cover plates have a relatively thick housing and are very dangerous to children because the chemical refill can easily be removed. The current invention uses a screw to securely lock all components and prevent children from touching chemical containing components. In addition, whereas the thicker body of the prior multiple function wall cover plates are too ugly because the multiple function components are added-on the existing wall cover plate, the current invention's concept is to replace the existing wall cover plate so that the thickness will be much less than that of the prior art. In particular, the current invention uses a conventional commercially available refill component which has the dimensions 6.5 cm (Length)×3.5 cm (Width)× 0.8 cm (Height) and simply installs it on the back housing to reduce thickness and improve appearance.

The current invention may incorporate (1) an air freshener, (2) a nightlight, which may include an electroluminescent (E.L.) element, LED, incandescent light, fiber optics, a fluorescent light, or a black tube, and related circuitry for the light source, and (3) a receptacle arrangement (which may include any number of receptacles) to let the wall cover plate offer the best functions to consumers.

Other prior art includes U.S. Pat. Nos. 6,716,256; 6,657, 380; 6,642,452; 6,413,598; 6,388,345; 6,342,995; 6,089, 893; 6,086,211; 6,050,716; 5,934,451; 5,899,549; 5,842, 763; 5,683,166; 5,670,776; 5,660,459; 5,637,930; 5,586, 879; 5,544,025; 5,485,356; 5,407,721; 5,117,734; 4,924, 349; 4,774,641; 4,755,913; 4,739,187; 4,617,613; 4,546, 419; 4,514,789; 4,255,780; 4,240,090; 4,038,582; and 3,895,225, as well as the Inventor's prior U.S. Pat. Nos. 6,280,053; 6,171,117; 6,170,958; and 6,183,101. None of these prior art patents discloses a multiple function wall cover plate having a plurality of functions including (1) fragrance(s), (2) receptacle(s), and (3) nightlight(s) to easily replace the original wall outlet's cover plate and provide electricity delivery from the prong(s) of the multiple functions wall cover plate as in the current invention described below, and in particular, a multiple function wall cover plate having the shape and thickness of an existing wall outlet and a safety screw to prevent children from touching any parts of a refill, the nightlight, or the receptacle.

BRIEF DESCRIPTION OF THE DRAWINGS

FIGS. 4-16 show preferred embodiments with an assortment of optional different outlet devices or electric devices, including an LED light device, EL light device, fluorescent tube device, power fail light device, illumination device, WiFi device, Internet device, wireless router device, timepiece, motion sensor device, remote control device, Bluetooth device, video camera device, recording device, memories means, digital data storage means, power means, energy saving means, energy storage device, batteries, DC power means, conductive means, prong means, electric parts, other accessories, optics means, reflective means, and optical light-traveling means to cause the wall cover to have more than two functions in addition to the USB means and light means.

DETAILED DESCRIPTION OF THE PREFERRED EMBODIMENTS

FIGS. 4-16 show preferred embodiments in which a selection of optional outlet devices or electrical devices, such as an LED light device, EL light device, fluorescent tube device, power fail light device, illumination device, WiFi device, Internet device, wireless router device, timepiece, motion sensor device, remote control device, Bluetooth device, video camera device, recording device, memories, digital data storage means, power means, energy saving means, energy storage device, batteries, DC power means, conductive means, prong means, electric parts and accessories means. optics means, reflective means, and optical light traveling means, enable the wall cover to have more than two built-in functions in addition to the USB means and light means.

Each of the wall covers shown in FIGS. 4-16 may have built-in USB and light means, with additional electric functions selected from the functions of the electrical devices listed above. Each different wall cover has different multiple-functions.

The wall covers of FIGS. 4-16 have the option to add more functions. Each of these embodiments uses a screw to fasten the multiple function wall cover on an existing outlet's screw hole(s) to fix the position. The multiple wall cover plate can therefore replace the existing non-functional wall cover plate, or overlay on top of the existing wall cover, because the electric delivery from the inner receptacle to the multiple wall cover are made by conductive means, illustrated in the preferred embodiment as a prong means with or without a ground pole.

Electric power delivery from inner wall receptacle though the prong-means to the multiple function wall cover utilizes a circuit to supply the AC electric signal to a multiple function circuit board to cause the multiple function circuit board to carry out pre-determined functions.

Figure 16:
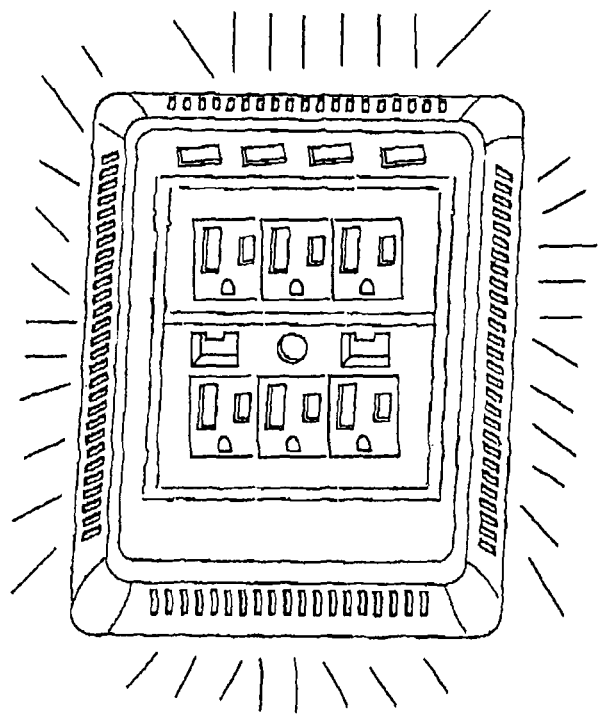

As shown in FIG. 16, the multiple functions wall cover plate can have a bigger size than the existing wall cover so that it can cover the whole area of the existing wall cover and its respectively hole on the wall. The current multiple function wall cover plate should not be smaller than the existing wall cover plate, but it will be appreciated that any size bigger than the existing wall cover plate should still fall within the scope of the current invention. The multiple function wall cover plate of the current invention may also overlay at least one of the inner AC wall outlet's receptacles depending on market requirements.

The embodiments of FIGS. 4-16 may also incorporate a wire arrangement as long as there exists a space with some wire hold-means (not shown), The wire can be well arranged within the space to prevent a mess. It is appreciated that any of the features described in the inventor's prior art or copending applications and patents may also be included without departing from the scope of the invention.

The embodiments of FIGS. 4-16 may therefore include, without limitation any of the following combinations of features:

1. A multiple function wall cover plate arranged to be installed on a wall outlet that includes at least one electrical receptacle mounted in a wall plate holder, comprising:

at least one front cover and a back base assembled to the front cover to form the multiple function wall cover plate, wherein the multiple function wall cover plate is fastened by a screw extending through the at least one front cover to the wall plate holder;

at least one electrical conductor arranged to supply electricity from the electrical receptacle to at least one electrical power output device, the electrical conductor extending rearwardly into the electrical receptacle, and the at least one electrical power output device including at least one USB port or multiple electrical power outlets, the at least one electrical power output device being arranged to receive one of a USB plug, prongs, an adaptor, or a contact of at least one external electric or digital data device;

at least one light source installed between the front cover and the back base to emit light and thereby provide lighting effects whenever the rearwardly extending electrical conductor is supplied with power from the receptacle and the at least one light source is turned on under control of a controller that includes of at least one of a sensor, switch, photosensor, motion sensor, power fail sensor, Bluetooth sensor, integrated circuit, and electrical circuit; and at least one additional function-providing device installed within the multiple function wall cover plate, the additional function-providing device including one of an additional electrical outlet, electrical device, LED light device, electroluminescent light device, fluorescent tube light device, power fail light device, illumination device, WiFi device, Internet device, wireless router, timepiece, motion sensor, remote control, Bluetooth device, video camera, recording device, digital data storage device, and power supply device.

2. A multiple function wall cover plate, wherein the at least one light source is one of an LED, electroluminescent light source, and fluorescent tube connected to the controller to exhibit predetermined light functions, performance, or effects.

3. A multiple function wall cover plate, wherein the multiple function wall cover plate covers at least one of a plurality of the electrical receptacles mounted in the wall plate holder.

4. A multiple function wall cover plate, wherein the at least one electrical power output device is a USB charging port.

5. A multiple function wall cover plate, wherein the at least one electrical power output device includes at least two additional electrical power output receptacles.

6. A multiple function wall cover plate, wherein the at least one electrical conductor supplies power to the at least one light source and the at least one additional function-providing device in addition to the at least one electrical power output device.

7. A multiple function wall cover plate, wherein the at least one electrical conductor includes at least one of a prong to be inserted into the receptacle and conductive elements selected from wires, metal conductive elements, solder, resilient conductive elements, and combinations of wires, metal conductive elements, solder, and resilient conductive elements.

8. A multiple function wall cover plate, comprising:
at least one front cover and a back base assembled to the front cover to form the multiple function wall cover plate, wherein the multiple function wall cover plate is fastened by a screw extending through the at least one front cover to a wall plate holder;
at least one electrical conductor arranged to supply electricity from the electrical receptacle to at least one electrical power output device, the electrical conductor extending rearwardly into the electrical receptacle, and the at least one electrical power output device including at least one USB port or multiple electrical power outlets, the at least one electrical power output device being arranged to receive one of a USB plug, prongs, an adaptor, or a contact of at least one external electric or digital data device;
at least one light source installed between the front cover and the back base to emit light and thereby provide lighting effects whenever the rearwardly extending electrical prong is inserted to the receptacle and the at least one light source is turned on under control of a controller that includes of at least one of a sensor, switch, photosensor, motion sensor, power fail sensor, Bluetooth sensor, integrated circuit, and electrical circuit; and
at least one additional electrical device.

9. A multiple function wall cover plate, wherein the additional electrical device is one of a:
 a. video or audio device
 b. lighting device;
 c. insect repeller;
 d. timepiece;
 e. motion sensor;
 f. infrared sensor;
 g. Bluetooth electrical device controller;
 h. WiFi device, router, or Internet device; and
 i. wire arrangement device.

10. A multiple function USB wall cover plate, comprising:
at least one front cover and a back base assembled to the front cover to form the multiple function wall cover plate, wherein the multiple function wall cover plate is fastened by a screw extending through the at least one front cover to a wall plate holder or held in place on a wall outlet by conductive or plastic prongs or poles;
at least one electrical conductor arranged to supply electricity from an electrical receptacle to a USB port, the front cover including an opening through which a plug of an external USB device is inserted into the USB port;
at least one light source installed between the front cover and the back base to emit light and thereby provide lighting effects whenever the rearwardly extending electrical prong is inserted to the receptacle and the at least one light source is turned on under control of a controller that includes of at least one of a sensor, switch, photosensor, motion sensor, power fail sensor, Bluetooth sensor, integrated circuit, and electrical circuit; and
at least one additional electrical device.

The following is a description of the wall cover plate of FIGS. 1, 1A, 2, 2A, 2B, and 3, shown in the inventor's U.S. Pat. No. 7,318,653, details of which may be included in the wall cover plate of FIGS. 4 to 16: The multiple function wall cover plate (10) of FIG. 2 has at least one ventilation area (11) (11 a) to allow the inside refill's fragrance (not shown) to be spread out to the environment, and at least one nightlight area (12) (12 a) (12 b) that incorporates a light source which may be selected from the group consisting of an electro-luminescent (EL) element, LED, incandescent light, neon light, fluorescent tube, black tube, gas filled light source, or any equivalent light source to offer a nightlight function. The light source is preferably connected to the power source by prongs, contact means (15) (15 a), and circuit means (not shown). The multiple function wall cover plate includes at least one pair of receptacles (14) (14 a) to keep the existing wall outlet functions without reducing the number of receptacles while adding multiple functions to the wall cover plate.

The multiple function wall cover plate has a center screw hole (18) to allow the multiple function wall cover plate to be securely fastened by a screw though the original outlet's screw hole and replace the original outlet's wall cover plate. The multiple function wall cover plate also has at least one pair of prong sets which can be easily inserted into the original wall outlet's receptacle and supply electricity from the original wall outlet to the multiple function wall cover plate's receptacle or receptacle(s) which, depending on market requirements, may be arranged to number from two receptacles to any number of receptacles by simply varying the inner copper-piece design to provide the desired number of receptacles.

Figure 1:
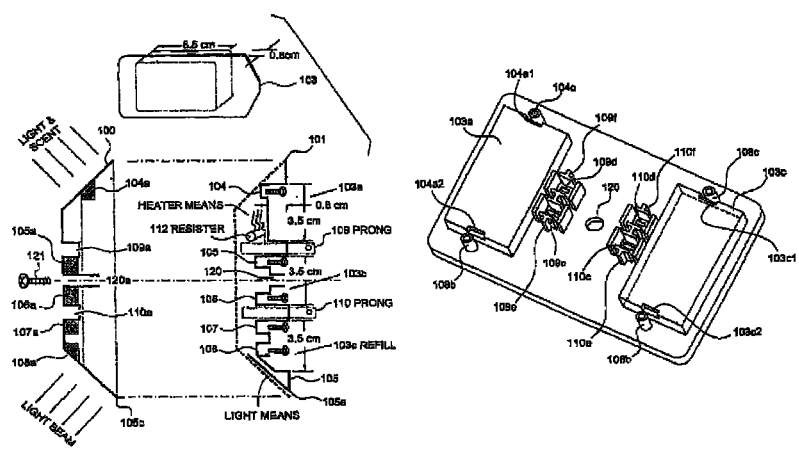
FIG. 1 is a side-view showing the front cover and back base of the wall cover plate disclosed in the inventor's U.S. Pat. No. 7,318,653.

As shown in FIG. 1, the front cover (100) and back base (101) are positioned and fastened by screws (104 b) (105 b) (106 b) (107 b) (108 b) through the passages (104) (105) (106) (107) (108) and held by the plastic posts (104 a) (105 a) (106 a) (107 a) (108 a). The back base (101) has at least one groove having dimensions of 3.5 cm×6.5 cm located at preferred locations (103 a) (103 b) (103 c) to allow the refill (103) to fit into the back base (101). The copper means (109) (110) are configured to allow current delivery from the original receptacle to the multiple function wall cover plate's receptacle. Delivery may be from one original receptacle to multiple receptacles, for examples from 1 original receptacle to 1 or 2 or 3 . . . etc. receptacles. The copper means may be of a commercially available type. Because the back base (101) replaces the original wall outlet's cover, the back base (101) can be attached the wall outlet's receptacle surface as close as possible to reduce the overall height and get the best and thinnest thickness and appearance. The front cover (100) has a hole (120 *a*) to allow the screw (121) to pass through the hole (120) in the back base to fasten on the original wall outlet's screw holder (not shown). The copper means (109) (110) are well installed within the channels (109 *a*) (110 *a*) to meet the safety standard and are not reachable by consumer. The refill (103) may be located at a top (103 *a*), middle (103 *b*), or bottom (103 *c*) position, preferably as long as the width of the groove is at least 3.5 cm so that more than 1 refill can be installed to provide the longest and strongest fragrance dispenser result relative to any other prior art devices. At least one heater means (112) may be arranged on the top of a pair of the cooper means (109) or (110) so as to use the copper means to provide electricity and produce heat, thereby causing air in front of the refill surface to move up and let the refill's fragrance spread out as widely as possible while the electricity is connected. At least one light source (not shown) is well arranged within the gaps (105 *a*) within a support board (105) sealed inside the back base to prevent contact with the consumer and hold the light source at a perfect location. The light source may be selected from any combination of an electro-luminescent (E.L.) element, LED, fluorescent tube, black light, neon light, and/or other equivalent light means and related circuit means. The light source can be arranged at various locations according to market and technical requirements. For example, the light source can include the light sources described in the Inventor's U.S. Pat. Nos. 6,170,958 and 6,171,117, which use resilient conductive means of rubber or metal material or with extra conductive means such as wire, metal panel, strips, terminals to deliver electricity to the light source(s) means via copper mean(s). These skills are available from the Inventor's earlier patents and other prior art.

The preferred embodiment of the multiple function wall cover plate discussed above, which replaces the original wall outlet's wall plate, not only offers an air freshener dispenser function but also offers a nightlight, multiple receptacles, and more than one refill compartment within a compact space with quick electrical connection accomplished by simply inserting the current invention's copper means into the original wall outlet's receptacle(s) without touching any hot wires. The preferred embodiment is, however, only one example and is not intended to be limiting. Advantages of the preferred embodiment include: (a) The wall cover plate has a configuration similar to that of the existing wall outlet cover plate. (b) The current invention's wall cover plate has a most compact thickness to allow a commercially available refill to be well installed without creating a new refill to cause the consumer to purchase a variety of refills. (c) The fragrance, light source, and receptacle(s) are all sealed within the front cover and back base. Furthermore, alternative or optional features may including such as: (1) The current receptacles may range in number from 2 receptacle(s) increase to any number of receptacles such as 3, 4, 5, 6 . . . N. (2) The refill number can be increased from 1 to 2, 3, 4, 5, . . . N. (3) The copper means/conductive means can be designed to provide a desired receptacle number (4) The front cover and back base can be made into a certain number of pieces that provide a curved shape or appearance. (5) The seal means for the front cover and back base can be selected from a screw(s), glue, sonic sealing, hot sealing, chemical sealing, catch and hook, notch, melting, or any other conventional sealing arrangement. (6) The light source may be selected from any combination of an E.L element, LED, incandescent bulb, neon light, fluorescent tube, black light, gas filled bulb, halogen lamp, or an equivalent light with desired brightness and power consumption. (7) The electric connection between the light means may be any conductive means or combination thereof, including resilient conductive means such as conductive rubber or a conductive spring, metal piece, wire, copper strips, bracket, metal plate or any combination with a clip, soldering, rivet, welding, snapping or equivalent procedure to deliver electricity from one end to the other ends. (8) The functions can be increased or reduced depend on market requirements. In addition, provision of less than the current three major functions of fragrance, nightlight, and receptacles may still fall within the current invention scope. For example, one may replace any one of the receptacle(s), nightlight(s), fragrance(s) functions with other functions or components such as a time piece(s), bug repelled device(s), blue tooth electric controller(s), remote controller(s), infrared sensor(s), and/or other electric related device(s) and still fall within the scope of invention, which is a multiple functions wall cover plate that replaces an original wall outlet plate. For a new building or house, the builder can adapt the multiple function wall cover plate of the current invention to provide a high-tech addition that greatly increases the house value.

Figure 1A:
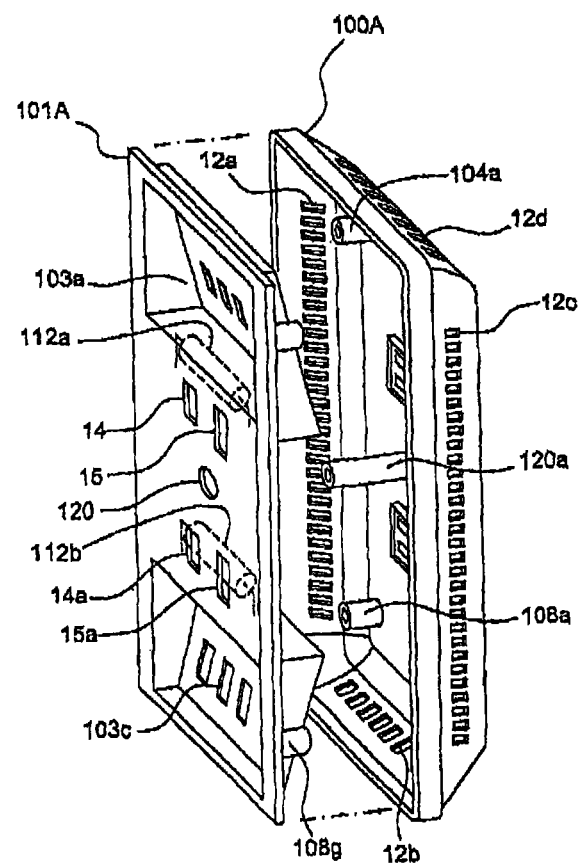
FIG. 1A is a side-view showing the construction of an alternative spatial arrangement of the wall cover plate of U.S. Pat. No. 7,318,653.

FIG. 1A shows an alternative design for the back case (101A) with only two refill compartments (103 *a*) and (103 *c*). Two wider prong holes (15) (15 *a*) are located on the left side of the back case. The two narrow prong holes (14) (14 *a*) are located on the right side of the back case. The central screw (not shown) can pass though the plastic tunnel (120 *a*) and opening (120) to fasten with the outlet device's screw holder (not shown). The refill compartment (103 *a*) (103 *c*) may have a lot of openings, cutouts, windows, holes, or grills to allow the refill's scent to pass through the back case (101A) to front cover (100A) and spread out from the front cover's grills, openings, cutout, windows, windows, and/or holes (12 *a*) (12 *b*) (12 *c*) (12 *d*) as quickly as possible. The heater means (112 *a*) (112 *b*) may be installed adjacent to the prong means (not shown) so provide electricity to cause hot air to flow up and bring the scent to a wider area. One or more heater means can be provided depending on market requirements. The light means can be installed within the front cover and back case with proper installation means.

Figure 2:
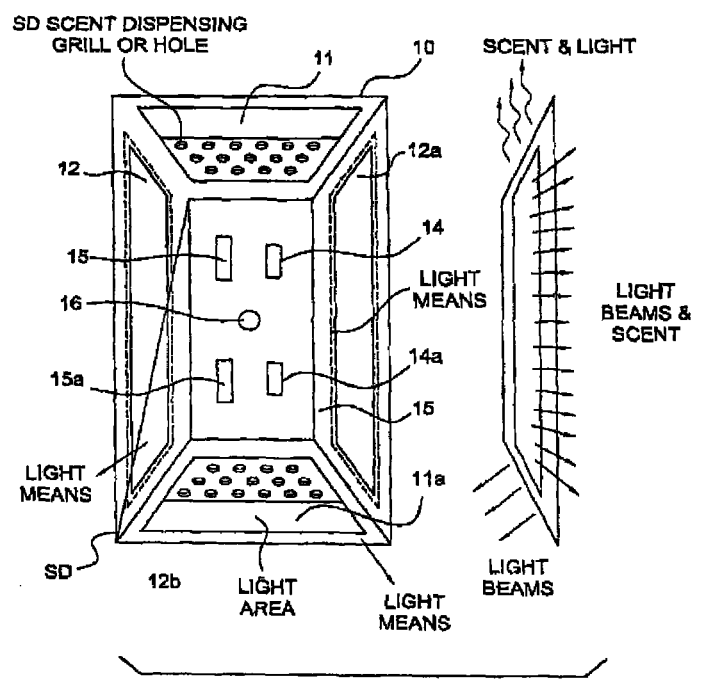
FIG. 2 is a front view showing scent flowing and light beam emitting directions of the wall cover plate of U.S. Pat. No. 7,318,653.
Figure 2A:
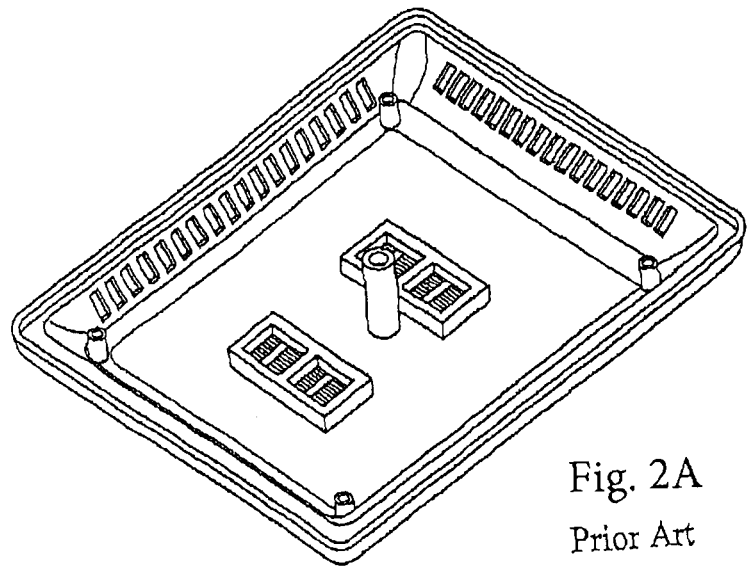
FIGS. 2A and 2B are a front view and back view of the wall cover plate of U.S. Pat. No. 7,318,653.
Figure 2B:
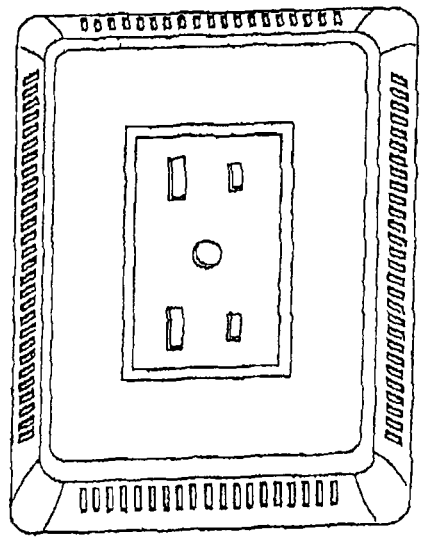

FIGS. 2A and 2B show details of the preferred front cover (10) with alternative openings, grills, windows, cutouts to allow the scent or smell of the refill to spread out quickly. These openings, grills, windows, or cutouts also can allow the light means to emit light out to a viewer. FIGS. 2-1 shows an alternative design of the front cover of FIG. 2 and can be varied as desired. FIGS. 2-2 sows the detailed construction of the inner side shown in FIG. 2.

Figure 3:
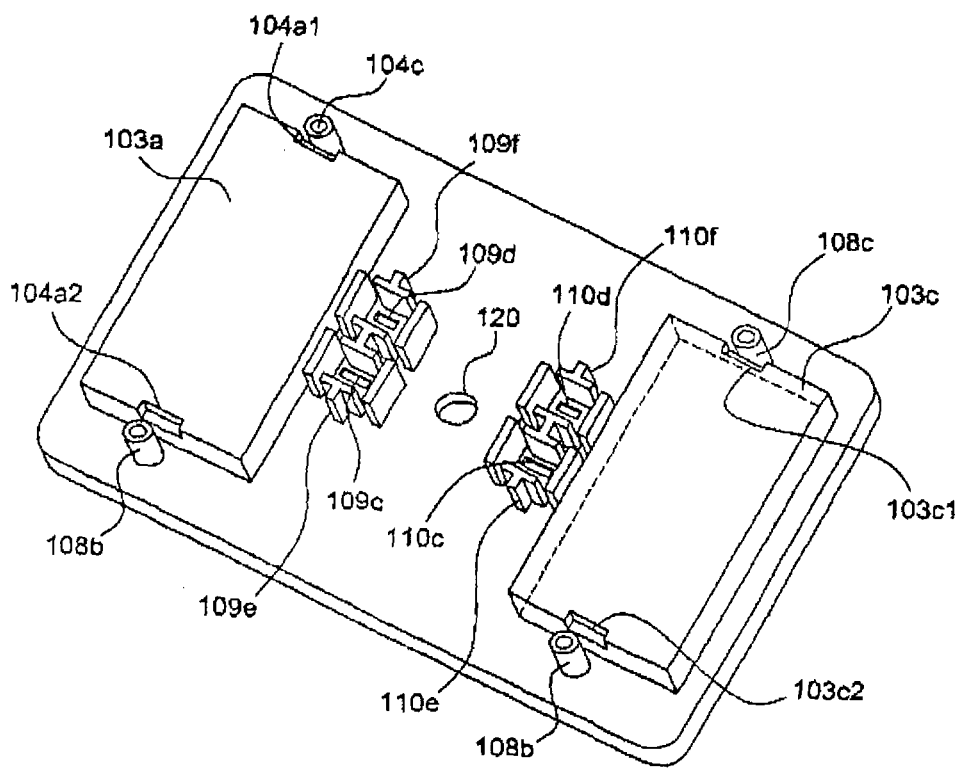
FIG. 3 is a perspective view of the inner side of the back plate of U.S. Pat. No. 7,318,653.
Figure 10:
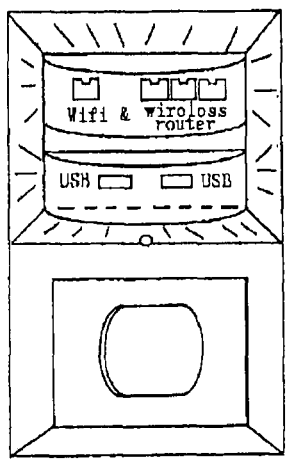
Figure 11:
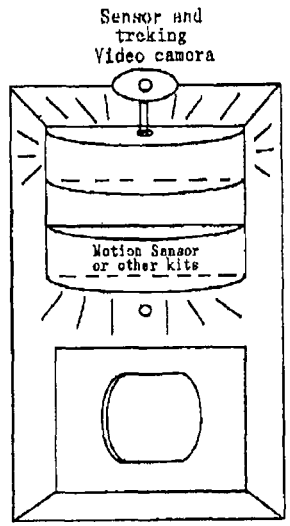
Figure 12:
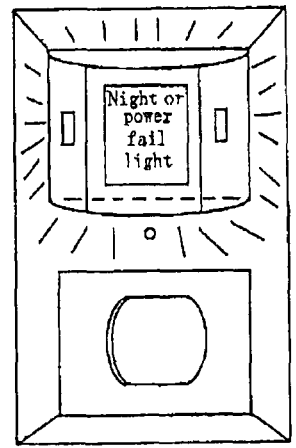
Figure 13:
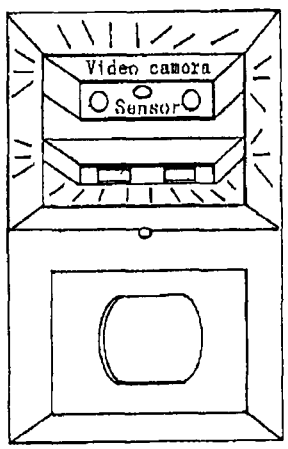
Figure 14:
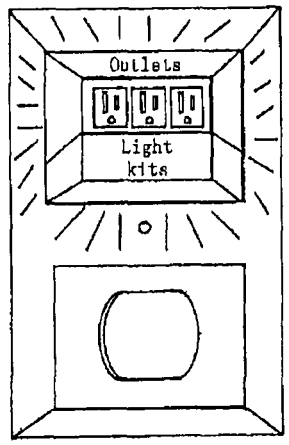
Figure 15:
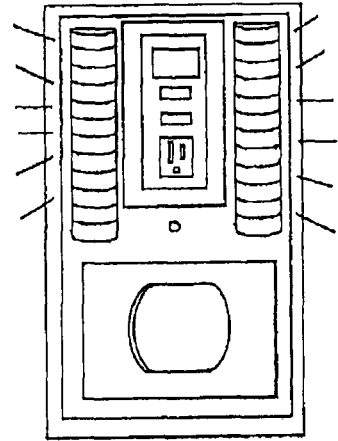

FIG. 3 shows in detail the construction of the preferred back case (101) of FIG. 1. The two refill compartments (103 *a*) (103 *c*) include screw stands (104 *c*) (104 *b*) (108 *c*) (108 *b*) to allow screws (not shown) to pass though and fasten with the front cover (not shown). The prong means are located at the prong holes (109 *c*) (109 *d*) (110 *c*) (110 *d*) which are surrounded by the walls (109 *e*) (109*f*) (110 *e*) (110*f*). The center screw hole (120) allows a longer screw (not shown) to pass through and be tightly fastened with the outlet device's screw holder.

The above discussed are not intended to limit the scope of the current invention. All alternatives, variations, equivalent functions, and minor changes still fall within the scope of the current invention. For example, the number of prong means can be at least one pair under some special requirements and still can supply power to two receptacles depending on the design of copper means/conductive means, and the copper means/conductive means also can be have any configuration as long as it supplies electricity as necessary. Furthermore, as described above, the light means may include any available light means and installation without departing from the scope of the current invention. The attachment means, fastening means, and installation means also may be varied without departing from the scope of the invention.

The invention claimed is:

1. A multiple function wall cover plate, comprising:
   at least one front cover and a back base assembled to the front cover to form the multiple function wall cover plate, wherein the multiple function wall cover plate is fastened by a screw extending through the at least one front cover to a wall plate holder located in a recess in a wall;
   at least one prong arranged as a power input to supply electricity from an electrical receptacle to at least one electrical power output device, said at least one prong extending rearwardly into the electrical receptacle, and the at least one electrical power output device including at least one USB port, and at least one additional electrical power outlet, or at least three additional electrical power outlets, said at least one electrical power output device being arranged to receive at least one of a USB plug, prongs, an adaptor, electrical signal receiver, or a contact of at least one external electric or digital data device;
   at least one light source installed between the front cover and the back base to emit light and thereby provide lighting effects whenever said at least one prong is supplied with power from said receptacle and said at least one light source is turned on under control of a controller that includes of at least one of a sensor, switch, photosensor, motion sensor, power fail sensor, Bluetooth sensor, wireless system, WiFi system, integrated circuit, and electrical circuit; and
   in addition to said at least one electrical power output device and said at least one light source, at least one additional function-providing device installed within the multiple function wall cover plate, wherein said at least one additional function-providing device is a device other than a power output device, said additional function-providing device including one of an additional electrical device, LED light device, power fail light device, illumination device, WiFi device, Internet device, wireless router, timepiece, motion sensor, remote control, Bluetooth device, video camera, recording device, and digital data storage device,
   wherein the wall cover plate further includes at least one opening configured to receive a male plug of another electrical device and enable the male plug to pass through the wall cover plate into the electrical receptacle to receive AC power therefrom.

2. A multiple function wall cover plate as claimed in claim 1, wherein said at least one light source is an LED connected to exhibit predetermined light functions, performance, or effects.

3. A multiple function wall cover plate as claimed in claim 1, wherein said multiple function wall cover plate covers at least one of a plurality of said electrical receptacles mounted in said wall plate holder.

4. A multiple function wall cover plate as claimed in claim 1, wherein said at least one electrical power output device is a USB charging port.

5. A multiple function wall cover plate as claimed in claim 1, wherein said at least one electrical power output device includes at least two additional electrical power output receptacles.

6. A multiple function wall cover plate as claimed in claim 1, wherein said at least one prong supplies power to said at least one light source and said at least one additional function-providing device in addition to said at least one electrical power output device.

7. A multiple function wall cover plate as claimed in claim 1, wherein said at least one wall cover plate includes said at least one prong to be inserted into said receptacle, and also conductive elements to connect to each said electrical power output device and selected from wires, metal conductive elements, solder, resilient conductive elements, and combinations of wires, metal conductive elements, solder, and resilient conductive elements.

8. A multiple function wall cover plate, comprising:
   at least one front cover and a back base assembled to the front cover to form the multiple function wall cover plate, wherein the multiple function wall cover plate is fastened by a screw extending through at least one hole in the wall cover plate to a wall plate holder located behind the wall cover plate;
   at least one prong arranged as a power input to supply electricity from an electrical receptacle to at least one electrical power output device, said at least one prong extending rearwardly into the electrical receptacle, and the at least one electrical power output device including at least one USB port, at least one USB port and at least one additional electrical power outlet, or at least three additional electrical power outlets, said at least one electrical power output device being arranged to receive at least one of a USB plug, prongs, an adaptor, electrical signal receiver, or a contact of at least one external electric or digital data device;
   at least one light source installed between the front cover and the back base to emit light and thereby provide lighting effects whenever said rearwardly extending electrical conductor is inserted to said receptacle and said at least one light source is turned on under control of a controller or circuitry that includes of at least one of a sensor, switch, photosensor, motion sensor, power fail sensor, Bluetooth sensor, wireless system, WiFi system, integrated circuit, and electrical circuit; and
   in addition to said at least one electrical power output device and said at least one light source, at least one additional electrical device other than a power output device.

9. A multiple function wall cover plate as claimed in claim 8, wherein the additional electrical device is one of a:
   a. video or audio device
   b. lighting device;
   c. insect repeller;
   d. timepiece;
   e. motion sensor;
   f. infrared sensor;
   g. Bluetooth electrical device controller;
   h. WiFi device, router, or Internet device; and
   i. wire arrangement device.

10. A multiple function USB wall cover plate, comprising:
   at least one front cover and a back base assembled to the front cover to form the multiple function wall cover plate, wherein the multiple function wall cover plate is fastened by a screw extending through at least one hole in the wall cover plate to a wall plate holder or held in place by conductive or plastic bars, prongs or poles;

at least one prong arranged as a power input to supply electricity from an electrical receptacle to at least one electrical power output device including a USB port, the front cover including an opening through which a male USB plug of an external USB device is inserted into the USB port;

at least one light source installed between the front cover and the back base to emit light and thereby provide lighting effects whenever said at least one prong is inserted to said receptacle and said at least one light source is turned on under control of a controller or circuitry that includes of at least one of a sensor, switch, photosensor, motion sensor, power fail sensor, Bluetooth sensor, wireless system, WiFi system, integrated circuit, and electrical circuit; and in addition to said at least one electrical power output device and said at least one light source, at least one additional electrical device other than a power output device.

11. A multiple function wall cover plate as claimed in claim 10, wherein the additional electrical device is one of a:

a. video or audio device
b. lighting device;
c. insect repeller;
d. timepiece;
e. motion sensor;
f. infrared sensor;
g. Bluetooth electrical device controller;
h. WiFi device, router, or Internet device; and
i. wire arrangement device.

* * * * *